(12) United States Patent
Holvoet et al.

(10) Patent No.: US 9,049,881 B2
(45) Date of Patent: Jun. 9, 2015

(54) **NUTRITIONAL COMPOSITION COMPRISING *LACTOCOCCUS* STRAINS AND REDUCING ALLERGY SYMPTOMS, ESPECIALLY IN INFANTS AND CHILDREN**

(75) Inventors: Sebastien Holvoet, Savigny (CH);
Annick Mercenier, Bussigny (CH);
Adrian Zuercher, Bern (CH); Anurag Singh, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/391,174

(22) PCT Filed: Aug. 13, 2010

(86) PCT No.: PCT/EP2010/061803
§ 371 (c)(1),
(2), (4) Date: Feb. 17, 2012

(87) PCT Pub. No.: WO2011/020780
PCT Pub. Date: Feb. 24, 2011

(65) Prior Publication Data
US 2012/0148629 A1  Jun. 14, 2012

(30) Foreign Application Priority Data

Aug. 18, 2009 (EP) .................................. 09168053
Sep. 17, 2009 (EP) .................................. 09170599

(51) Int. Cl.
| | | |
|---|---|---|
| A61K 35/74 | (2006.01) |
| A61P 37/04 | (2006.01) |
| A61P 37/08 | (2006.01) |
| A23L 1/29 | (2006.01) |
| A23K 1/00 | (2006.01) |
| A23K 1/16 | (2006.01) |
| A23K 1/18 | (2006.01) |
| A23L 1/30 | (2006.01) |
| A23L 1/305 | (2006.01) |
| A23L 1/308 | (2006.01) |

(52) U.S. Cl.
CPC ............. *A23L 1/296* (2013.01); *A23K 1/009* (2013.01); *A23K 1/1634* (2013.01); *A23K 1/1643* (2013.01); *A23K 1/1806* (2013.01); *A23K 1/1846* (2013.01); *A23L 1/3014* (2013.01); *A23L 1/3053* (2013.01); *A23L 1/3055* (2013.01); *A23L 1/308* (2013.01); *A23V 2002/00* (2013.01); *A61K 35/74* (2013.01)

(58) Field of Classification Search
None
See application file for complete search history.

(56) References Cited

U.S. PATENT DOCUMENTS

| | | | |
|---|---|---|---|
| 2006/0263344 A1 | 11/2006 | Skop | |
| 2008/0299255 A1* | 12/2008 | Kim et al. | ............. 426/51 |
| 2008/0305089 A1 | 12/2008 | Bufe | |

FOREIGN PATENT DOCUMENTS

| | | |
|---|---|---|
| CN | 1149969 | 5/1997 |
| CN | 101484024 | 7/2009 |
| CN | 101594789 | 12/2009 |
| EP | 862863 A2 * | 9/1998 |
| EP | 1239032 | 9/2002 |
| EP | 1538198 | 6/2005 |
| EP | 1858336 | 11/2007 |
| EP | 2009007515 | 1/2009 |
| GB | 2077101 | 12/1981 |
| JP | 55022641 | 2/1980 |
| JP | 2004018469 | 1/2004 |
| JP | 2006028050 | 2/2006 |
| JP | 2009060800 | 3/2009 |
| WO | 9700078 | 1/1997 |
| WO | 2006097415 | 9/2006 |
| WO | 2006697949 | 9/2006 |
| WO | 2009082214 | 7/2009 |

OTHER PUBLICATIONS

Gill H S et al: "Dietary Probiotic Supplementation Enhances Natural Killer Cell Activity in the Elderly: An Investigation of Age-Related Immunological Changes"; Journal of Clinical Immunology, vol. 21, No. 4, Jul. 1, 2001, pp. 264-271, XP019281030.
Moreau M-C: "Fermented milks: probiotic effects on host's immunity?" Sciences Des Aliments, vol. 26, No. 6, Jan. 1, 2006, pp. 517-524, XP009139747.
Christophe P Frossard et al: "Oral administration of an IL-10 secreting *Lactococcus lactis* strain prevents food induced IgE sensitization" Journal of Allergy and Clinical Immunology, vol. 119, No. 4, Apr. 1, 2007, pp. 952-959, XP002555795.
Pal Kaur I et al: "Probiotics: delineation of prophylactic and therapeutic benefits"; Journal of Medicinal Food, vol. 12, No. 2, Jan. 1, 2009, pp. 219-235, XP009139754.
PCT International Search Report for International Application No. PCT/EP2010/061803 with a Mailing Date of Oct. 22, 2010, 6 pages.
Akiyama et al., "Dietary unripe apple polyphenol inhibits the development of food allergies in murine models," FEBS letters, vol. 579 (2005), pp. 4485-4491.

* cited by examiner

*Primary Examiner* — Robert A Zeman
(74) *Attorney, Agent, or Firm* — K&L Gates LLP (57) ABSTRACT

A complete nutritional composition comprising *Lactococcus* strains or probiotic is provided for reducing the symptoms of allergies in different groups of patients such as allergies originating from food allergens in young children or infants and respiratory allergens in children, adults and household pets. Preferably the composition reduces symptoms of allergies (secondary prevention) while not significantly affecting sensitization (primary prevention). The composition comprises a probiotic of the genus *Lactococcus*.

4 Claims, 9 Drawing Sheets

Figure 1 / Table 1. Cytokine secretion by Th2-skewed human PBMC after co-culture with *Lactococcus* strains

|  | Cytokine production (% of reference) | | |
| --- | --- | --- | --- |
|  | IFNγ [a] | IL-10 [b] | IL-5 [c] |
| *L. lactis* NCC 2287 (SL131) | 274.1 | 97.4 | 51.5 |
| *L. lactis* NCC 2180 (SL60) | 86.2 | 53.0 | 40.8 |
| *L. plantarum* NCC 1107 (Lp8) | 29.4 | 5.7 | 19.1 |

[a] Amount of IFNγ induced by stimulation with purified *E. coli* LPS = 100%

[b] Amount of IL-10 induced with a reference bacterial strain with proven ability to induce IL-10 = 100%

[c] Amount of IL-5 induced in absence of any stimulation (medium) = 100%.

Figure 2 / Table 2. mRNA expression by Th2-skewed human PBMC after co-culture with *Lactococcus lactis* NCC 2287 (SL131)

| | mRNA level (relative expression)[a] | | | | | |
|---|---|---|---|---|---|---|
| | medium | | LPS | | NCC 2287 (SL131) | |
| | 10 h | 24 h | 10 h | 24 h | 10 h | 24 h |
| IFNγ | 32 | 72 | 168 | 163 | 18249 | 3034 |
| IL-10 | 24 | 29 | 20 | 17 | 1243 | 91 |
| Tbet | 38 | 49 | 57 | 44 | 194 | 77 |
| IL-5 | 22 | 38 | 6 | 11 | 63 | 8 |
| GATA-3 | 65 | 81 | 33 | 51 | 64 | 39 |

[a] relative expression is based on levels of 3 housekeeping genes

Figure 3:

Figure 3: Schematic description of OVA food allergy model

Figure 4:

Figure 4: Reduced symptoms of food allergy in mice receiving $5 \times 10^8$ CFU/ml in drinking water of *L. lactis* NCC 2287 (SL131) during the last week before challenge but not in mice receiving the same strain during the sensitization phase or in mice receiving probiotic strain *L. plantarum* NCC 1107 (Lp8). Results of 2 independent experiments. Solid line corresponds to median, dotted line corresponds to mean.

Figure 5:

Figure 5: Median levels of Mouse Mast-Cell Protease 1 (MMCP-1) in sera 4 hours after challenge. Solid line corresponds to median, dotted line corresponds to mean.

Figure 6 / Table 3. Cytokine production by mesenteric lymph nodes lymphocytes and splenocytes restimulated *ex vivo*

|  | Cytokine production by MLN (pg/ml) | | | | | | | |
|---|---|---|---|---|---|---|---|---|
|  | IL-1 | IL-2 | IL-4 | KC | TNFα | IFNγ | IL-5 | IL-10 |
| Neg. Control | 45.8 | 349 | 6.6 | 53.9 | 345.3 | 31.9 | 12 | 96.1 |
| Pos. Control | 107.5 | 1062.9 | 97.6 | 206 | 333 | 703.7 | 73.9 | 475.3 |
| SL131[a] | 79.5 | 1013.6 | 56.6 | 255.7 | 251.5 | 317.9 | 73.2 | 330.5 |

|  | Cytokine production by splenocytes (pg/ml) | | | | | | | |
|---|---|---|---|---|---|---|---|---|
|  | IL-1 | IL-2 | IL-4 | KC | TNFα | IFNγ | IL-5 | IL-10 |
| Neg. Control | 269.9 | 950.4 | 39.8 | 555.9 | 327.7 | 1945.5 | 31.6 | 417 |
| Pos. Control | 295.4 | 1225.5 | 184.1 | 764.9 | 349.5 | 3472.8 | 188 | 789.6 |
| SL131[a] | 246 | 916 | 76.9 | 647.6 | 241 | 1324.9 | 89.9 | 499.1 |

Results from 1 representative experiment are shown.
[a] *L. lactis* NCC 2287 (SL131) was given to sensitized mice in drinking water for 1 week before challenge.

Figure 7 / Table 4. Gene expression levels in ileum

| Target gene | Relative gene expression (median±SEM and fold change) | | | | | |
|---|---|---|---|---|---|---|
| | Neg Control | | Pos Control | | NCC 2287 (SL131)[a] | |
| | Relative[b] | Fold[c] | Relative[b] | Fold[c] | Relative | Fold[c] |
| IL-4 | 6±1 | 1 | 16±84 | 2.5 | 13±8 | 2.1 |
| IL-13 | 6±1 | 1 | 648±360 | 100.5 | 48±62 | 7.4 |
| CCL11 | 4703±3286 | 1 | 18038±6797 | 3.8 | 4638±1341 | 1.0 |
| CCL17 | 359±177 | 1 | 3754±888 | 10.5 | 1568±521 | 4.4 |
| IL-10 | 306±163 | 1 | 2604±1540 | 8.5 | 912±1154 | 3.0 |
| IL-12a | 100±148 | 1 | 830±438 | 8.3 | 36±630 | 0.4 |
| IFN-γ | 775±308 | 1 | 1747±738 | 2.3 | 251±395 | 0.3 |

[a] *L. lactis* NCC 2287 (SL131) was given to sensitized mice in drinking water for 1 week before challenge.
[b] Relative gene expression levels were normalized to 3 house keeping genes (GAPDH, β-actin, HPRT)
[c] Fold expression was normalized to expression levels in the Neg Control group Figure 8: Cytokine production in PBMC isolated from patients suffering from respiratory allergy and cultured *ex vivo* with *L. lactis* NCC 2287 (SL131) with or without grass pollen allergen. Solid line corresponds to median values.

Figure 9: Cytokine production in whole blood cells isolated from both patients suffering from respiratory allergy and non-allergic subjects and cultured *ex vivo* with *L. lactis* NCC 2287 (SL131). Solid line corresponds to median values.

NUTRITIONAL COMPOSITION COMPRISING *LACTOCOCCUS* STRAINS AND REDUCING ALLERGY SYMPTOMS, ESPECIALLY IN INFANTS AND CHILDREN

CROSS REFERENCE TO RELATED APPLICATIONS

The present application is a National Stage of International Application No. PCT/EP2010/061803, filed on Aug. 13, 2010, which claims priority to European Patent Application No. 09168053.8, filed on Aug. 18, 2009, and European Patent Application No. 09170599.6, filed Sep. 17, 2009, the entire contents of which are being incorporated herein by reference.

FIELD OF THE INVENTION

This invention relates to the use of probiotics, especially *Lactococcus* strains in the manufacture of a nutritional composition for reducing the allergic symptoms in allergic patients when exposed to allergens.

BACKGROUND TO THE INVENTION

Allergies are among the most common health problems affecting the life of patients of all age. Allergic diseases are nowadays recognized as an epidemic by the World Health Organization. The prevalence of allergies has been shown to increase in the past decades. Modern life style, especially urban, has been associated with high prevalence and higher severity of allergic manifestations. Allergic sensitization in childhood, especially in early childhood and especially to food allergens, is critical and of highest interest as development of an "allergic phenotype" or "atopy" has been shown to facilitate subsequent sensitization to other allergens. Hence allergies in childhood can be the first step of an allergic cascade leading to multiple allergies later in life, a process commonly referred to as "The Atopic March". For example, it has been demonstrated in human cohorts that children with persistent food hypersensitivity early in life have a dramatically increased risk to develop allergic rhinitis (hay fever) or asthma later in childhood (Ostblom et al 2008). Children with milder forms of food hypersensitivity also have increased risk for development of respiratory allergies but to a lesser degree than children with persistent food hypersensitivity. Therefore, attenuating the severity of food hypersensitivity may be crucial for slowing down the "Atopic March". In this context the management of allergic episodes and prevention of allergies are, in childhood and infancy, of the highest importance.

The immune system of infants is actively developing all along the few first years of life. Acting on, preventing, avoiding, managing, reducing or modulating the allergic reactions in such young patients can influence their allergic profile short term but also longer term for later in life.

Prevention of Allergies can be Achieved on Different Levels:

"Primary prevention" is the effect of preventing or reducing the risk of sensitization of patients to allergens, characterized by absence or reduced levels of allergen-specific IgE antibodies. Preventing or reducing sensitization will result in absence or reduction of allergic symptoms upon exposure to the same allergen. By modulating the way a patient gets sensitized in regard to one allergen or one group of allergens (primary prevention), the subsequent allergic response may also be modulated.

"Secondary prevention" is the effect of modulating the symptoms of allergies, i.e. the occurrence or intensity of the allergic reaction in patient already sensitized to one or several allergens when the patient is re-exposed to said allergen(s). By modulating the occurrence or intensity of the allergic symptoms (secondary prevention), the inconvenience associated with allergies is minimized.

Given these distinct concepts of allergy prevention it may be hypothesized that by virtue of their inherent mechanisms of action, some compounds might act solely at one or at both of these specific levels of prevention. Some may, for example, solely reduce the sensitization to a specific allergen (primary prevention), while other compounds may solely have an effect on the secondary prevention and reduce the severity of allergic reactions. Other compounds may be able to influence both sensitization and symptoms and thus are effective in promoting primary and secondary prevention. Also, compounds that exert a beneficial effect in reducing symptoms of one form of allergy may or may not work for a different allergy caused by a different allergen.

Food allergens are among the first allergens that infants encounter in their early life: typically, cow's milk proteins may be encountered by infants not receiving exclusive breastfeeding. Milk-proteins are indeed among the most frequently observed causes for food allergy in infancy, followed by eggs and wheat proteins. In general, food allergies can manifest by cutaneous (rash, eczema, others) and gastrointestinal symptoms (abdominal cramps; pain, especially in the abdomen; vomiting) in infants and young children. Further sensitization and episodes of allergies can also appear when the infant/young child is exposed to a novel food such as cereals, vegetables, fruits, nuts or fish.

Respiratory allergens (so-called "airborn allergens") are ubiquitous. These can either be seasonal (such as pollen) or perennial (house dust mite, cockroach, pet dander, molds & fungi). They cause respiratory allergy symptoms that can manifest by nasal (runny nose, itching, sneezing, blockage/obstruction) or ocular symptoms (watery eyes, itching, redness) in children and adults.

Lactococci are traditional dairy starter lactic acid bacteria. It has been demonstrated that specific strains of lactococci can confer a health benefit and thus these strains may be regarded as probiotics under the definition of the WHO. For example, an anti-allergic effect has been ascribed to a particular strain of *Lactococcus*: Makoto Enomoto et al describe in GB2077101A (published on 16 Dec. 1981) an anti-allergic composition comprising "lactobacterium" belonging to the *Streptococcus* genus, which is the former designation of *Lactococcus* (i.e. *Streptococcus lactis* is now termed *Lactococcus lactis*).

Furthermore various probiotic cultures or mixes of probiotics have been described for their effect on the allergic immune system: for example EP1858336 (WO2006697949), describes a mix of probiotics that can decrease the risk of allergies due to wheat flour albumin and globulins. JP2006028050 describes the skin allergy suppressive properties of compositions comprising probiotic bacteria such as *Lactobacillus* and *Streptococcus*.

However there remains a need for specifically reducing allergic reactions and symptoms in the population of young children and infants. This is especially important when considering the maturation of both the intestinal and immune systems undergoing in young children and when considering the multiplicity of novel allergens that the young children are exposed to, especially around weaning.

The question of food born allergic reactions in the young age is even further complicated by the specific nutritional needs of infants and young children. Caloric intake, caloric density, variety of desirable nutrient, protein content and protein quality are all among the factors important to bring the most appropriate nutrition to infants and young children. The presence of micronutrients such as vitamins and minerals are also of importance, more specifically when their concentration is limited by specific recommended ranges corresponding to the age of the target patients. As such, for the young children and infants, the matrices of food delivery are inherently complex but they are also of less variety: for example infants, although potentially allergic, usually require a specific protein balance in a matrix of milk-derived proteins. The presence of such multiple nutrients can potentiate the effect of the food allergens. In such complex matrices, low key food allergens unable to trigger allergic manifestation alone can then become more powerful at initiating an allergic reaction. Similarly compounds that may neutralize allergens or act on allergy prevention may see their effect diminished or annihilated in such complex nutritional matrices. Specifically it is not predictable whether compounds usually recognized to act on allergy prevention would still be active, and to which extend, in complex matrices such as nutritional composition for infants or young children.

There is a need to bring relief in the symptoms of food allergies in populations of infants and young children that have a history of allergic episodes and/or are allergic.

There is a need to provide a complete nutritional composition that not only brings a variety of nutrients but also reduces the severity of allergic reactions.

There is a need for providing a nutritional composition modulating the allergic reaction of young patients suffering from light to moderate forms of allergies, as these patients have special needs dictated by the incomplete maturity of their intestinal and immune systems.

There is also a need for modulating allergic reactions in young children that do not tolerate stringent pharmaceutical molecules, for example by nutritional interventions such as including modulators of the immune system into the regular nutritional regimen.

There is a need for providing a nutritional composition modulating the allergic reaction of young patients at the time, and around the time of weaning when the intestinal tract undergoes substantial modification and when new solid foods, potentially containing new allergenic proteins, are introduced and hence the patient is particularly susceptible to the sensitization to food allergens.

There is a need for providing a nutritional composition to help better manage or reduce symptoms of respiratory allergy (i.e. air-born allergies) in children and adults upon exposure to seasonal (for example pollen) or perennial airborne allergens (for example house dust mite, cockroach, pet dander, molds & fungi).

There is a need for providing a complete nutritional composition that can restore the balance of the immune system in allergic patients and thus be effective in modulating the different symptoms of allergies (cutaneous, food, respiratory), especially in fragile, immune depressed or elderly patients.

There is a need for alleviating the symptoms of allergies by providing an effective composition, possibly by reducing the exposure to intact allergens, even though the composition may not directly reduce the sensitization to allergens.

There is a need for a composition that has a positive effect on secondary prevention of allergy while not necessarily acting on the primary prevention to the same allergies.

There is finally a need for a composition, most particularly suited for young patients that by reduction of symptoms can help to diminish the "allergic phenotype" and thus can lower sensitization later in life to new allergens. There is a need for attenuating the atopic march.

SUMMARY OF THE INVENTION

In a first aspect, the present invention provides a complete nutritional composition for reducing the symptoms of allergies originating in particular from food, in patients having allergies triggered by food allergens or other allergens, especially in young patients, babies and infants and especially effective at the time of weaning.

In a second aspect, the present invention provides a composition that significantly promotes secondary prevention of allergic reactions triggered by food allergens, optionally while not affecting the primary prevention against the same allergens.

In a third aspect, the present invention provides a composition that comprises probiotics, especially belonging to the *Lactococcus* genus.

In another aspect of the invention the composition of the invention is effective in reduction of allergic symptoms to airborne allergens in children and adults.

The invention can further provides a composition that restores the immune balance in allergic individuals and thus can be effective for different types of allergy.

The invention may have the particular benefit of reducing the allergies later in life.

DETAILED DESCRIPTION OF THE INVENTION

Definitions

In this specification, the following terms have the following meanings:

"Patients" means mammals including humans and animals especially common pets such as cats and dogs. The term patients include infants, children, teenagers, adults, fragile subjects, immune depressed subjects and/or elderly people or animals in the corresponding life stages.

"Complete nutritional composition" For the purpose of this document a complete nutritional composition is a composition that comprises a significant amount, usually 20% or more, of the major nutritional nutrients recommended for a given age. Such major nutrients are usually provided in quantity and proportion such as to fulfil 20% or more of the specific recommended nutrient's doses for a given age, when used in adequate quantity for providing the recommended caloric intake for a given age. A complete nutritional composition usually comprises a source of protein, a source of lipid, a source of carbohydrates in a balanced proportion that meets the general recommendation for a given age. It usually also include micronutrients such as vitamins and minerals, as well as a source of essential amino acids and a source of essential fatty acids. It is however understood that a complete nutritional composition may not comprise all specific nutrients, nor all recommended amounts, to fulfil all nutritional needs of an infant or young child. A complete nutritional composition excludes compositions comprising merely Lactococcus or Lactococcus in a predominant proportion.

"Symptoms of allergies" generally include symptoms triggered by allergens. Such symptoms include cutaneous (redness of skin, rash, itchiness, dermatitis, eczema), ocular (itching and watering of the eyes), gastrointestinal (congestion, abdominal pain, cramps, vomiting diarrhea), respiratory (itching of the nose, nasal congestion, rhinitis, asthma) and in severe cases systemic (dizziness, mental confusion, anaphylaxis) manifestations.

"Primary prevention of allergies" means all measures aiming at avoidance or reduction of allergic (immunological) sensitization for example prevention or reduction of specific IgE antibodies.

"Secondary prevention of allergies" means prevention or reduction of the development of allergic disease/allergic symptoms in a sensitized individual.

"Weaning period" is the period during which infants are adapting from pure liquid nutrition to solid or semi-solid food, and adapting from quasi unique food type (generally mother milk or infant formula) to a variety of foods.

"Sensitization" means induction/development of allergen-specific IgE antibodies.

"Immune boost" can be characterized by an increase in Th-1 cytokines mainly IFNγ that is needed to defend against harmful microbial exposures particularly in immune depressed individuals, without a concurrent increase in inhibitory cytokines such as IL-10.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10). The definition of probiotic is generally admitted and in line with the WHO definition. The probiotic can comprise a unique strain of micro-organism, of a mix of various strains and/or a mix of various bacterial species and genera. In case of mixtures the singular term "probiotic" can still be used to designate the probiotic mixture or preparation. For the purpose of the present invention, micro-organisms of the genus Lactococcus are considered as probiotics.

"Prebiotic" generally means a non digestible food ingredient that beneficially affects the host by selectively stimulating the growth and/or activity of micro-organisms present in the gut of the host, and thus attempt to improve host health.

"Airborn allergies" and "airborn allergens" are used as synonyms of respiratory allergens and respiratory allergies.

"Cutaneous allergies or skin allergies" are allergies whose symptoms affects the skin or coat, or whose action modes involves the skin or coat. They can include redness, rash or irritation of the skin.

Lactococcus lactis (L. lactis) strain NCC 2287 (Nestlé Culture collection) is the L. lactis strain with the alternative name of SL131 and the international identification reference CNCM-I-4154 (Collection Nationale de Cultures de Microorganismes at Institute Pasteur, Paris, France). Lactococcus lactis (L. lactis) strain NCC 2180 (Nestlé Culture collection) is the L. lactis strain with the alternative name of SL60 and the international identification reference CNCM-I-4199. Lactobacillus plantarum strain NCC 1107 (Nestlé Culture Collection) is the L. plantarum with the alternative name Lp8 and the international identification reference CNCM 1-4227. CNCM identifications refer to the Collection Nationale de Cultures de Microorganismes at Institut Pasteur, 22 rue du docteur Roux, 75724 Paris, France.

The inventors have evidenced that allergic reaction and symptoms can be alleviated when sensitized young mammals are provided with a complete nutritional composition that comprises L. lactis NCC 2287 (SL131). This defined a positive effect on the secondary prevention of allergies.

Surprisingly this effect was not accompanied by a reduction of the sensitization of the young mammals to allergens (i.e. no primary prevention of allergies was evidenced).

Effect of the Composition:

The invention relates to the use of microorganisms of genus Lactococcus, more particularly a specific strain of Lactococcus lactis, and more specifically strain NCC 2287 (SL131) for the manufacture of a complete nutritional composition for reducing the symptoms in patients having allergies triggered by food or airborne or skin allergens. The inventors have evidenced that consumption of Lactococcus in general and L. lactis NCC 2287 (SL131) in particular leads to reduced symptoms of food allergy in a group of mice receiving a nutritional composition containing said strain of Lactococcus. This is evidenced when an allergic reaction (challenge) is induced after sensitization. The model mimics food allergy in humans, when humans (typically infants/young children) are naturally sensitized to food allergens and further re-exposed to said allergens. The bacterial strain L. lactis NCC 2287 (SL131) hence shows a protective effect.

In one embodiment of the invention the effect of the composition is more specifically an effect on the secondary prevention of allergies. The symptoms of allergies, in the mouse model, are indeed reduced significantly, as illustrated by a lower allergic clinical score. Generally the symptoms can include all or a selection of the usually recognized symptoms of allergies.

In one embodiment of the invention the symptoms comprise diarrhea, skin irritation, inflammation of the intestinal tract, skin rash, skin irritation, ocular or respiratory symptoms or combinations thereof.

In one embodiment of the invention the symptoms are accompanied by release of biochemical mediators, such a tryptase, chymase, histamine, leukotrienes.

In one embodiment of the invention the composition however has no effect on the sensitization of the patients to the allergens. Indeed primary prevention seems not to be achieved by the composition comprising L. lactis NCC 2287 (SL131). The subjects are still sensitized to the food allergens, but develop less symptoms of allergy when re-exposed to the sensitizing allergen. Without being bound to the theory it is believed that the effect therefore does not reduce the natural immune defenses (which have a positive effect for the patient) but simply reduces the expression of the symptoms of allergy.

In one embodiment of the invention the composition significantly influences the immune response triggered upon exposure to airborne allergens. In response to stimulation by L. lactis NCC 2287 (SL131), PBMC's and whole blood cells of grass pollen allergic individuals secreted increased amounts of cytokines (IFNγ and IL-10) that are suggestive of a restoration of immune balance in allergic individuals. The composition thus has the added value of being effective for different allergic disorders triggered to a wide variety of allergens (food, airborne, cutaneous).

In one embodiment the composition of the invention comprises L. lactis NCC 2287 (SL131) and has an effective effect on reducing allergy symptoms, especially in patient suffering from food allergies, skin allergies or airborn allergies.

In one embodiment the composition reduces the sensitization to other allergens later in life. It is believed that the composition promotes (or at least does not block) the natural processes of immune maturation and hence, is able to have a long term effect on lowering the sensitization to the same allergens or to different allergens (reduction of sensitization later in life). By solely reducing the symptoms of allergy (secondary prevention), it is hypothesized that the composition of the invention can allow for the natural immune maturation to occur, and have such long term beneficial effect.

In one embodiment of the invention the composition inhibits immune responses to allergic triggers in different mammalian species. The composition can be used to reduce symptoms in species such as cats and dogs that are known to develop allergic reactions.

In one embodiment of the invention the composition inhibits allergic immune responses and concurrently boosts the levels of immune responses needed to fight harmful microbes. The composition can thus be effective in boosting immune function in fragile, elderly and hospitalized subjects.
Composition of the Invention or for Use in the Invention:

The composition of the invention can be a complete nutritional composition such as an infant formula or can bring a substantial portion of the complete diet. Preferably the composition is a complete nutritional composition that brings all or almost all the nutritional requirements of the target body when taken as the sole source of nutrient. In another embodiment, such as a baby food, the composition brings a portion of the complete diet, preferably 50% or more or 20% or more (quantitatively and qualitatively). In one embodiment the composition comprises infant cereals. In one embodiment the composition may be a liquid composition for children comprising cereals or a baby food. In one embodiment the composition comprises dairy products (powder or liquid) for children and adults. In one embodiment the composition comprises petcare/pet nutrition (dry and wet food, topical) products for household pets.

The probiotic used is of the *Lactococcus* genus. Although the inventors can not exclude that other probiotics would have a similar or related effect, no experimental data could prove that other genera or strains of probiotics are equally effective, besides the one observed for *B. longum*, in particular *B. longum* NCC 2705 described in the co-pending application by the same inventors.

In one embodiment of the invention the probiotic is strain *L. lactis* NCC 2287 (SL131). In one embodiment of the invention the strain is *L. lactis* NCC 2180 (SL60).

In one embodiment of the invention the composition comprise between $10^4$ and $10^{11}$ colony forming units (CFU) per g of the dry composition. When the composition is an infant formula the amount of probiotic in the infant formula can be between $10^5$ and $10^8$ CFU/g of infant formula. In one embodiment the composition comprises between $10^6$ and $5\times10^7$ CFU/g, that is in a dose demonstrated to have a physiological effect. In one embodiment it has been identified that probiotics at a low dose can have a beneficial effect, in particular when the composition also comprises prebiotics and proteins in a defined limited amount. In such embodiment the probiotics are present in the composition in an amount between $10^3$ and $10^5$ CFU/g. The prebiotics can by oligosaccharides and/or the proteins can be present in an amount not exceeding 4 g/100 kcal or less than 2 g/100 kcal or less than 1.8. g/100 kcal or less than 1.5 g/100 kcal of the composition.

The probiotic can be mixed together with the dry or wet composition of the invention. Treatments or specific processes can be applied to improve the stability or viability of the probiotics in the composition. The probiotic can be applied in a dry form or in a wet from After mixing the probiotic with the composition the mix can be processed in a way that does not dramatically affect the viability of the probiotics. In another embodiment the probiotics are partly or fully inactivated before, during or after the mixing. In one embodiment the probiotics have been rendered inactivated and/or incapable to replicate prior to the use in the composition of the invention. This for example can be achieved by heat treatment or other described treatments.

In one embodiment the probiotic is dead or non-replicating or has been inactivated such as to render it non replicating. The term probiotic also comprises the meaning of "parts or fragments of probiotic bacteria".

In one embodiment of the invention, the composition comprises prebiotics. It is known that prebiotics comprise carbohydrates and more specifically, oligosaccharides. Furthermore it is known that they have widely been used as functional food ingredients. They resist hydrolysis by enzymes of the human digestive tract, can reach the colon undegraded and provide a carbohydrate substance particularly suited to the growth of bifidobacteria or other probiotics. Oligosaccharides may for example be produced from glucose, galactose, xylose, maltose, sucrose, lactose, starch, xylan, hemicellulose, inulin, or a mixture thereof. Purified commercially available prebiotic products such as fructooligosaccharides contain greater than about 95% solids in the form of oligosaccharides.

Preferably, an embodiment of the composition is a nutritional composition which comprises at least one prebiotic.

Preferably, an embodiment of the prebiotic comprises an oligosachharide produced from glucose, galactose, xylose, maltose, sucrose, lactose, starch, xylan, hemicellulose, inulin, or a mixture thereof. More preferably the oligosaccharide comprises fructooligosaccharide. Most preferably the prebiotic comprises a mixture of fructooligosaccharide and inulin. Preferably this mixture comprises PREBIO1® or a mixture of commercially available RAFTILOSE® and RAFTILINE®.

Preferably, an embodiment of the prebiotic component of the composition comprises about 50% to about 90% fructooligosaccharide. More preferably it comprises about 60% to about 80% fructooligosaccharide. Most preferably it comprises about 70% fructooligosaccharide. Preferably, an embodiment of the prebiotic comprises about 10% to about 50% inulin. More preferably it comprises about 20% to about 40% inulin. Most preferably it comprises about 30% inulin. In one embodiment the prebiotic component may represent about between 0.1% and 10% of the composition.

In one embodiment, the composition of invention further comprises an apple extract comprising polyphenols. The apple extract can help reducing the symptoms of allergies originating from food in patients having allergies triggered by food allergens. As such the apple extract acts in a synergistic way with the probiotic *Lactococcus* in order to modulate, reduce, or attenuate allergies in patients having food allergies. In one embodiment such composition is used for baby food and/or baby cereals that naturally represent a suitable carrier for the composition. In a further embodiment the baby food or baby cereals comprises apple extracts or material from apple. In one embodiment of the invention the apple extract is the protein extract commercialized by Val de Vire Bioactives (Conde sur Vire, France) under the reference "Pomactiv HFV". In one embodiment the apple extract is similar to or derived from the cited Pomactiv HFV and has similar effect. In one embodiment the use of the apple extract, especially with *L. Lactis*, is of particular interest for children other than infants, teenagers, adults or animals such as cat and dogs at corresponding age phase.

Hypothetical Mechanism of Action:

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, without being bound by the theory, it is hypothesized that allergy can be mitigated, down-regulated or prevented by restoring an appropriate balance between the Th1 and Th2 arms of the immune system. This implies the necessity to reduce the Th2 responses or to enhance, at least transiently, the Th1 responses. The former could be characterized by reduced production of Th2 cytokines such as IL-5, the latter could be characterized by increased production of Th1 cytokines such as IFNγ.

In one embodiment of the invention the composition comprises hydrolyzed or partially hydrolyzed proteins. A nutritional composition based on (partially) hydrolyzed proteins is particularly suited to the immune system and gastro-intestinal tract of infants/young children because hydrolyzed proteins are more easily digested and have reduced allergenicity compared to intact proteins. Furthermore, without being bound by the theory it can be hypothesized that hydrolyzed proteins might be a preferable substrate for probiotics and intestinal bacteria (especially those displaying a variety of peptidase activities) compared to intact proteins, leading to an improved effect of the probiotic strain and thus synergism between hydrolyzed proteins and probiotics. This represents a most appropriate composition for the immune system and gastro-intestinal tract of a food-allergic infant/young child. In such instance the combination of *L. lactis* NCC 2287 (SL131) with hydrolyzed proteins is of highest relevance to the invention.

In one embodiment the hydrolyzed proteins are proteins hydrolyzed from whey and/or casein. In one embodiment the hydrolyzed proteins result from the action of trypsin and/or chymotrypsin on the proteins (esp. whey proteins). In one embodiment the hydrolyzed proteins comprise soy proteins or/and egg proteins. In one embodiment the hydrolyzed proteins results from the action of proteases such as PROTAMEX® and/or FLAVOURZYME® (Novozyme, Denmark).

In one embodiment the proteins of the composition, preferably the hydrolyzed proteins, comprise cereal or eggs proteins. In one embodiment the hydrolyzed proteins results from the action of Alcalase. The composition of the invention can comprise a mix of 2 or more of the cited protein sources.

Target Group:

The composition of the invention is suitably targeted for different categories of patients: Those include, either relatively young patients that develop symptoms to food allergens and young patients and adults that have allergic manifestations to airborne or contact allergens. Other mammalian species (especially non human mammals or household pets such as cats, dogs or horses but may also include rabbits, guinea-pigs, hamsters, mice, piglets, lions, tigers or rats) that react to similar allergens could also benefit from the composition. Preferentially for food allergies the patients are sufficiently young to still going through a maturation phase of their immune system and their gastro-intestinal tract. In such patients the effect of the composition can be more intense or more rapid. In one embodiment the composition is an infant formula, infant cereal and/or a baby food. Preferably the composition is targeted at young humans below the age of 6 years, between birth and the age of 3 years or between birth and weaning. In one embodiment the composition is a starter or a follow-up infant formula. Preferably the nutritional composition comprises a vast majority of the necessary nutrients for the feeding of the young humans.

In one embodiment the nutritional composition is an infant cereal composition for infants/young children 1 to 4 years old. The composition can be more specifically targeted to and administered during the weaning period and/or up to 12 months thereafter. The weaning period is indeed important in regard to the invention as the infants are exposed to a variety of foods during the weaning period, while still undergoing maturation and re-organisation of their immune system and their gastro-intestinal tract. Effective control of the allergic response is therefore of particular importance during that period.

In regard to the use of the composition of the invention the children, babies or infants can be allergic children. Allergic children are those children, babies or infants having experienced at least one episode of allergic reaction—light, moderate or severe—to a food allergen. In one embodiment of the invention the children, babies or infants have declared severe allergies to food allergens and/or have experienced more than one moderate or severe episode of food allergy. The symptoms of allergies can include various known symptoms such as cutaneous irritation or redness, gastro-intestinal symptoms or respiratory symptoms.

The food allergens encompassed by the present invention can include all types of allergens naturally occurring or usually occurring in food, especially food for young humans (e.g. infants, babies, children). In another embodiment the food allergens are most commonly found in older children's, teenager's and adult's food.

In one embodiment the nutritional composition is a composition for children and adults that suffer from respiratory allergies. The respiratory allergens encompassed by the present invention can include all types of allergens that are airborne, can be seasonal (for example pollen) or perennial (for example house dust mite, cockroach, pet dander, molds & fungi). It is understood that infants may be particularly sensitive to the air-born allergens—by immediate effect or effect later in life (by "education" of the immune system).

In one embodiment the nutritional composition is a composition for other non human mammalian species. Such animals may include cats, dogs or horses and may also include rabbits, guinea-pigs, hamsters, mice, piglets, lions, tigers or rats) Those animals may develop different manifestations of allergic symptoms.

In one embodiment the nutritional composition is a composition for providing immune boost in fragile, hospitalized and elderly adults that have a depressed immune status.

In one embodiment the composition of the invention is a nutritional composition for adults, elderly or fragile patients. Preferably, in one example, the composition is a nutritional composition having a complete amino-acid profile, carbohydrates, lipids and micronutrients (such as vitamins), such as to be sufficient to fulfil the caloric and qualitative needs of fragile patients. In one embodiment the composition is an enteral composition intended for tube feeding in patients not absorbing solid food.

Experimental Results, Section 1:

Probiotics, predominantly belonging to the genera *Lactobacillus* and *Bifidobacterium* have been tested in human and animal trials for their ability to interfere with allergic sensitization or with development of allergic symptoms in sensitized individuals. Here we addressed whether bacteria of the genus *Lactococcus* have potential to mitigate development of allergic sensitization or symptoms. Specifically, we tested the characteristics and the effect of *Lactococcus lactis* NCC 2287 (SL131) and *Lactococcus lactis* NCC 2180 (SL60).

In an initial step we developed and used an in vitro system based on human blood lymphocytes to determine cytokine profiles induced by *Lactococcus*. We hypothesized that the observed profiles would be predictive for cytokine production induced in vivo by the same strains and thus for the biological effects conferred by said strains.

Cells of an allergic individual or of an individual prone to allergy development are characterized by their propensity to produce Th2 cytokines. To partly mimic this status in vitro, we developed a cell culture model of Th2-skewed human peripheral blood mononuclear cells (PBMC) as an alternative to using PBMC of allergic donors. Th2-skewing was induced by culturing PBMC with interleukin (IL)-4+anti-CD40 antibody as detailed in the Methods section. As a basic read-out the cytokines IFNγ, IL-10 and IL-5 were measured by ELISA in the supernatant of cells stimulated with *Lactococcus*.

Figure 1:
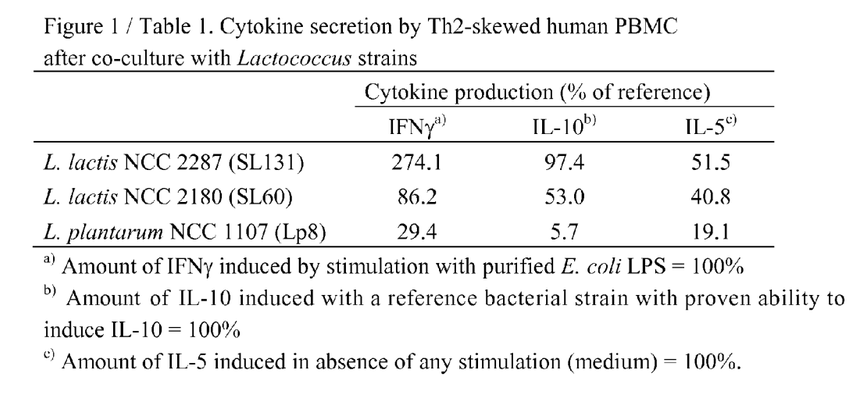
FIG. 1/Table 1: Cytokine profile of Th2-skewed human PBMC after co-culture with *Lactococcus lactis* NCC 2287 (SL131) deposited by Nestec S.A. under CNCM I-4154, *Lactococcus lactis* NCC 2180 (SL60) CNCM I-4199 or *Lactobacillus plantarum* NCC 1107 (Lp8) CNCM I-4227. Human peripheral blood mononuclear cells were Th2-skewed with IL-4 and anti-CD40 antibody for 3 days, then bacterial strains were added. Supernatants were harvested on day 5, cytokines were measured by ELISA.

FIG. 1/table 1 shows that *L. lactis* NCC 2287 (SL131) strongly induced secretion of IFNγ and IL-10, concomitant with inhibition of IL-5 secretion. Similarly, *L. lactis* NCC 2180 (SL60) induced IFNγ and IL-10 production and inhibition of IL-5 secretion. For comparison, another candidate probiotic strain, namely *Lactobacillus plantarum* NCC1107 (Lp8)) induced only low levels of IFNγ and IL-10, but was a good inhibitor of IL-5 production.

Figure 2:
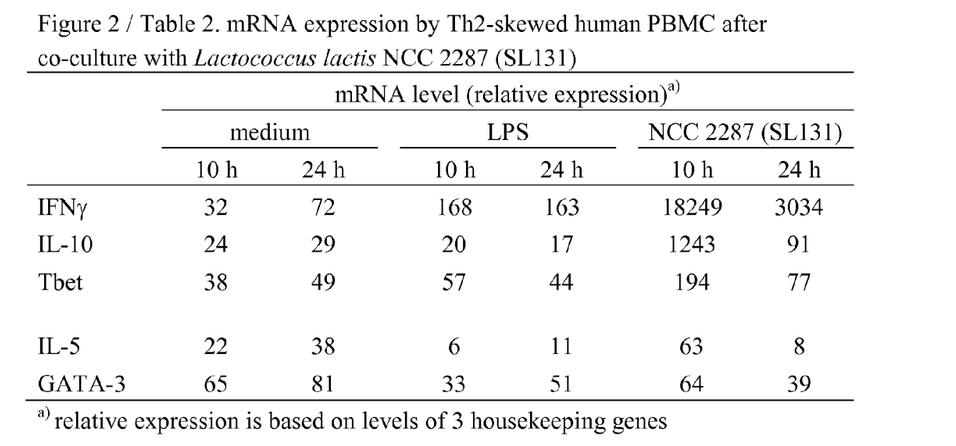
FIG. 2/Table 2: mRNA profile of Th2-skewed human PBMC after co-culture with *L. lactis* NCC 2287 (SL131). Human peripheral blood mononuclear cells were Th2-skewed with IL-4 and anti-CD40 antibody for 3 days, then *L. lactis* NCC 2287 (SL131) was added. Cells were harvested 10 h and 24 h thereafter, mRNA expression levels were measured with qRT-PCR.

FIG. 2/Table 2 shows confirmation of these results for *L. lactis* NCC 2287 (SL131) on the mRNA level. Expression levels of various genes were analysed 10 and 24 hours after starting co-cultures of Th2-skewed human PBMC with *L. lactis* NCC 2287 (SL131), LPS or no stimulus.

Culture of Th2-skewed PBMC with *L. lactis* NCC 2287 (SL131) led to strong induction of IFNγ and IL-10 mRNA (FIG. 2.) The peak of mRNA expression was reached after 10 hours of co-culture with *L. lactis* NCC 2287 (SL131). Following a similar expression profile, mRNA for Tbet, a master regulator transcription factor for Th1 cytokines, was induced by *L. lactis* NCC 2287 (SL131). A medium-low level of mRNA was induced by LPS stimulation, whereas the transcription levels in unstimulated cultures (medium) fluctuated only marginally. After *L. lactis* NCC 2287 (SL131) stimulation IL-5 mRNA transcription increased for a brief period after culture initiation before being strongly inhibited and dropping below levels of non-treated Th2 cells (medium). A similar mRNA expression profile was noted for GATA-3, a master regulator transcription factor for Th2 cytokines. Altogether, these findings confirm the results obtained on the protein level (FIG. 1/Tab 1.)

Figure 3:
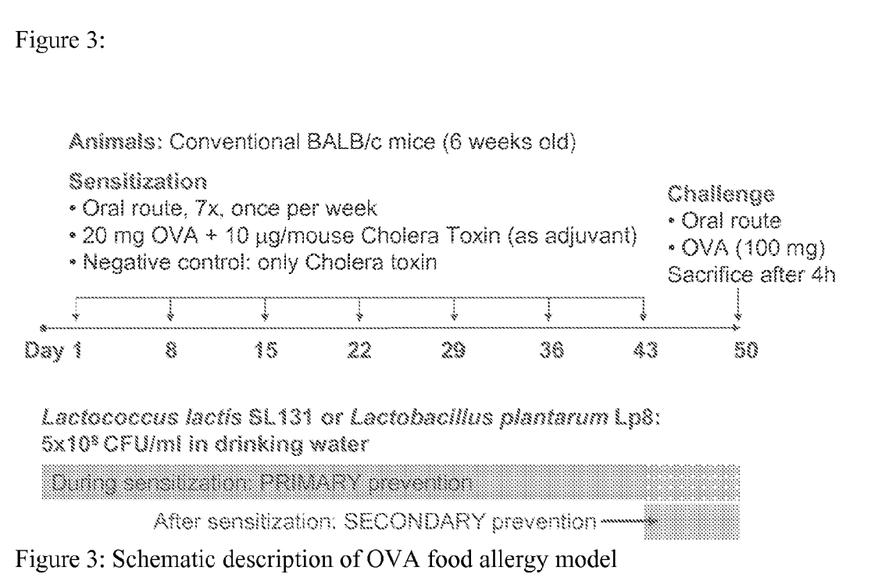
FIG. 3: Schematic description of OVA food allergy mouse model

The in vivo effect of *L. lactis* NCC 2287 (SL131) was tested in a mouse food allergy model (OVA Food Allergy Mouse Model, illustrated in FIG. 3). BALB/c mice were sensitized at weekly intervals with ovalbumin (OVA)+cholera toxin by the oral route during 7 weeks. In this model, oral challenge with a large dose of OVA at the end of the sensitization period leads to clinical symptoms such as diarrhoea, scratching episodes, bristled fur, cyanosis and loss of mobility.

*L. lactis* NCC 2287 (SL131) ($5\times10^8$ CFU/ml; ad libitum) was given to mice via drinking water during the sensitization phase from day 1 to 43 or 50 (primary prevention) or during the last week of the experiments (day 43-50; secondary prevention).

Figure 4:
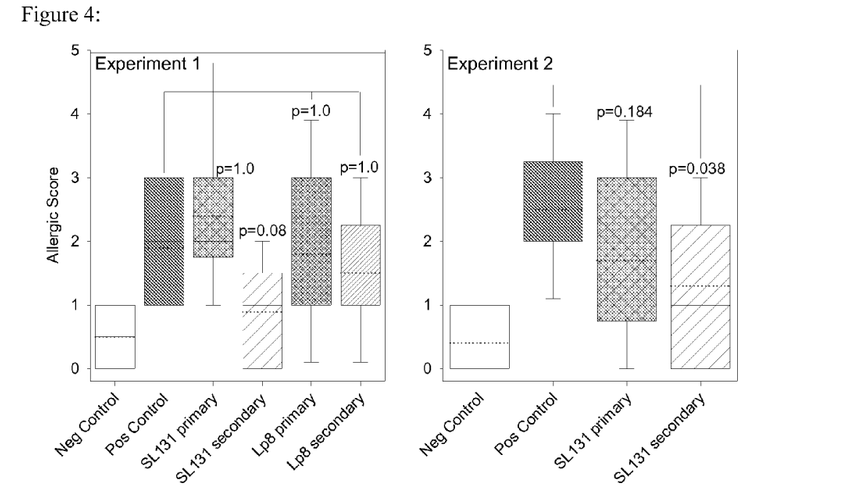
FIG. 4: Reduced symptoms of food allergy in mice receiving $5 \times 10^8$ CFU/ml of *L. lactis* NCC 2287 (SL131) or *L. plantarum* NCC 1107 (Lp8) either during sensitization period (primary) or during the last week before allergen challenge (secondary). Results of 2 independent experiments.

FIG. 4 shows the clinical symptoms observed in two individual experiments, After challenge mice treated with *L. lactis* NCC 2287 (SL131) during the last week of the experiment (secondary prevention) developed less severe clinical symptoms than sensitized, untreated animals (Positive Control). Mice consuming *L. lactis* NCC 2287 (SL131) during the sensitization phase of the experiment (primary prevention) did not exhibit reduced symptoms. In experiment 1, *L. plantarum* NCC 1107 (Lp8) was tested in parallel to *L. lactis* NCC 2287 (SL131). Neither in primary nor in secondary prevention did this strain reduce allergic symptoms, which was in accordance with our in vitro hypothesis.

Figure 5:
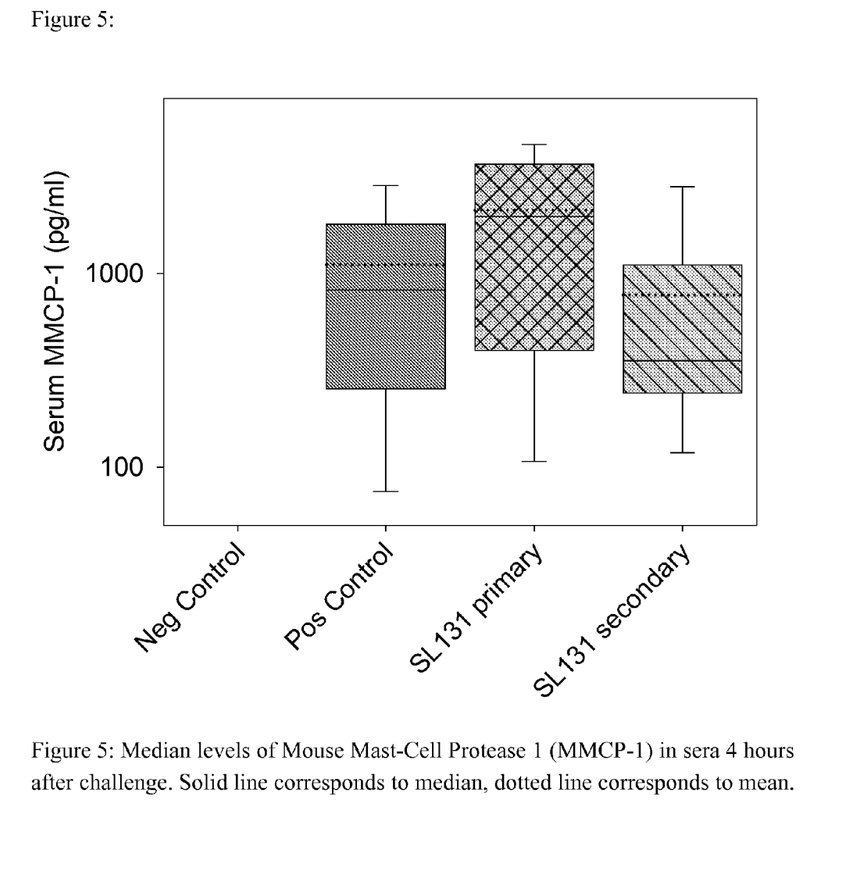
FIG. 5: Median levels of Mouse Mast-Cell Protease 1 (MMCP-1) in sera 4 hours after challenge.

As shown in FIG. 5, in addition to the clinical score, mouse mast-cell protease 1 (MMCP-1) serum levels were determined as a measure of intestinal mast-cell activation by allergen challenge. Consumption of *L. lactis* NCC 2287 (SL131) in secondary prevention reduced MMCP-1 serum levels compared to non-treated control animals (FIG. 5). Treatment with *L. lactis* NCC 2287 (SL131) in primary prevention did not influence the serum levels of MMCP-1.

Figure 6:
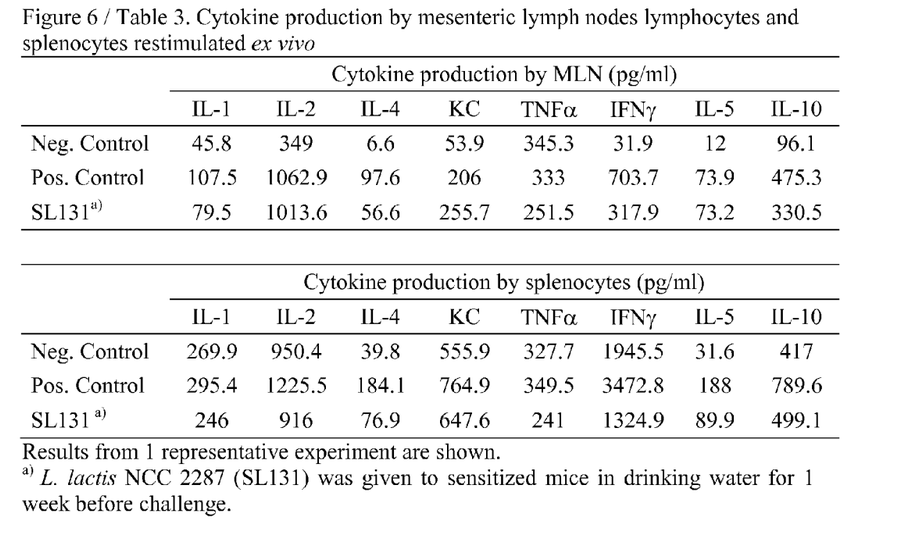
FIG. 6/Table 3: Cytokine production by mesenteric LN lymphocytes and splenocytes restimulated ex vivo.

FIG. 6/Table 3 shows cytokine production by ex vivo restimulated lymphocytes. For this purpose, lymphocytes from mesenteric lymph nodes (MLN) were collected after challenge, restimulated with 1 mg/ml of OVA and cultured for 72 hours. Levels of IL-1, IL-2, IL-4, KC, TNFα, IFN-γ, IL-5 and IL-10 were measured by multiplex assay (MESOS-CALE®). MLN lymphocytes of *L. lactis* NCC 2287 (SL131)-treated mice produced less IL-4, TNFα, IFN γ and IL-10 compared to the Positive Control (Tab. 3). Similarly, splenocytes secreted reduced levels of IL-2, IL-4, TNFα, IFN-γ, IL-5 and IL-10.

Figure 7:
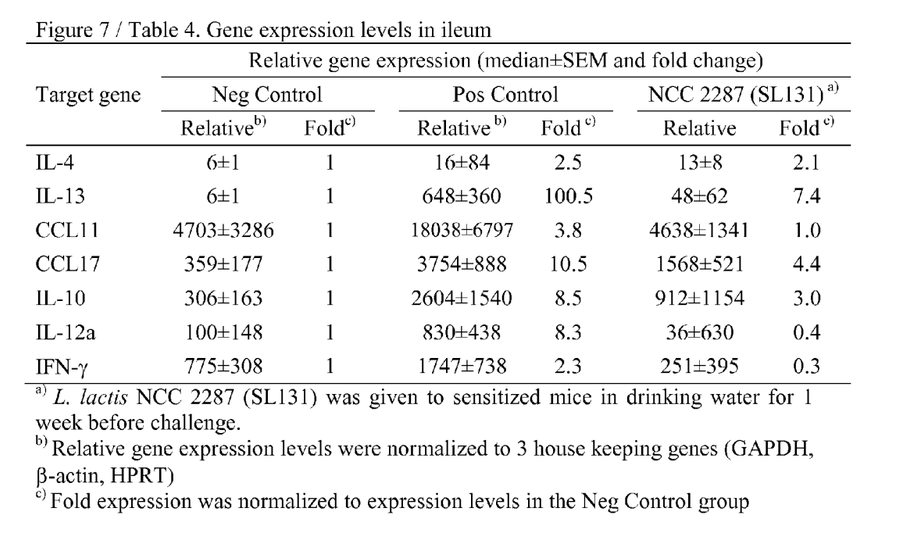
FIG. 7/Table 4: Gene expression levels in ileum isolated 4 hours after challenge.

Expression levels in the intestine of various genes associated with allergy were determined by quantitative real-time polymerase chain-reaction (qRT-PCR—see method below). The measurements of gene expression were performed on tissues from ileum for the positive control group, the negative control group and the group receiving *L. lactis* NCC 2287 (SL131) during the last week before challenge (secondary prevention). FIG. 7/Table 4 illustrates the results obtained: The group receiving *L. lactis* NCC 2287 (SL131) exhibited a reduced expression of various genes, including cytokines interleukin (IL)-13, IL-10, interferon (IFN)-γ and chemokine CCL11 (eotaxin) in ileal Peyer's Patches and cytokines IL-13, IL-10, IL-12, IFN-γ, chemokines CCL11 (eotaxin) and CCL17 (TARC) in ileum. A marked increased of the chemokine receptor CCR3 was observed. The genes for which reduced expression has been evidenced are generally recognized markers for a T helper 2 phenotype (IL-13, CCL11, CCL17), which is known to drive development of allergies. Hence the experiments demonstrate the downmodulation of immune responses by reduction of expression of relevant genes when the sensitized animals received *L. lactis* NCC 2287 (SL131) (secondary prevention). This is believed to be contributing to the anti-allergic effect of the tested strain of *Lactococcus* in the reduction of allergic symptoms (secondary prevention).

Experimental Results, Section 2:

Different probiotics strains have previously been examined for their beneficial effect in different allergic disorders. A bacterial strain that exerts a probiotic effect against skin or food allergy may or may not be effective in reducing allergic symptoms triggered by airborne allergens (see in particular: J. Nutr. 2010 March; 140(3):713S-21S. e-pub 2010 Feb. 3). The present experiments address whether *L. lactis* NCC 2287 (SL131) had the potential to exert a probiotic effect on responses triggered via respiratory allergens in addition to its observed beneficial effect on food allergies. The effect of NCC 2287 (SL131) on respiratory allergies was evaluated in human ex vivo assays, utilizing either PBMCs or whole blood cells from grass pollen allergic individuals.

Figure 8:
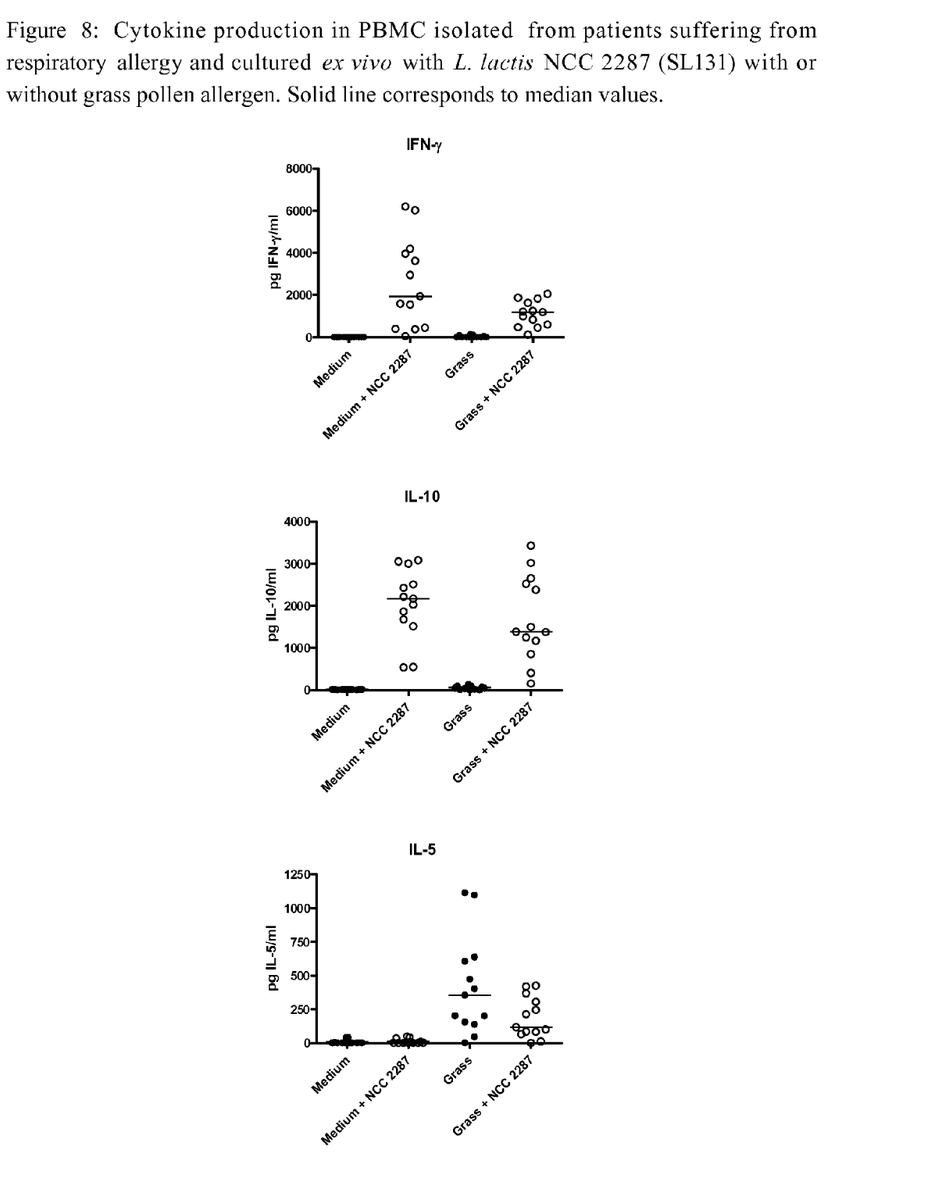
FIG. 8: Cytokine production by Peripheral Blood Mononuclear Cells (PBMC's) from grass pollen allergic individuals in medium or in the presence of grass allergen pollen extract (ALK-Abello wässrig 6 grass). After 2 days of culture, NCC 2287 (SL131) was added at $10^7$ CFU/ml. PBMC culture was continued for an additional 3 days resulting in total culture duration of 5 days.

FIG. 8 shows the effect of NCC 2287 (SL131) on PBMC isolated from grass pollen allergic individuals. Correlating well with previously observed results in the Th-2 skewed assay, *L. lactis* NCC 2287 (SL131) induces a strong production of IFNγ and IL-10 from allergic PBMC. Upon restimulation with mix of grass allergens ex vivo, *L. lactis* NCC 2287 (SL131) was shown to exert a similar beneficial effect where it increased IFNγ and IL-10 and concurrently inhibited IL-5 levels.

Figure 9:
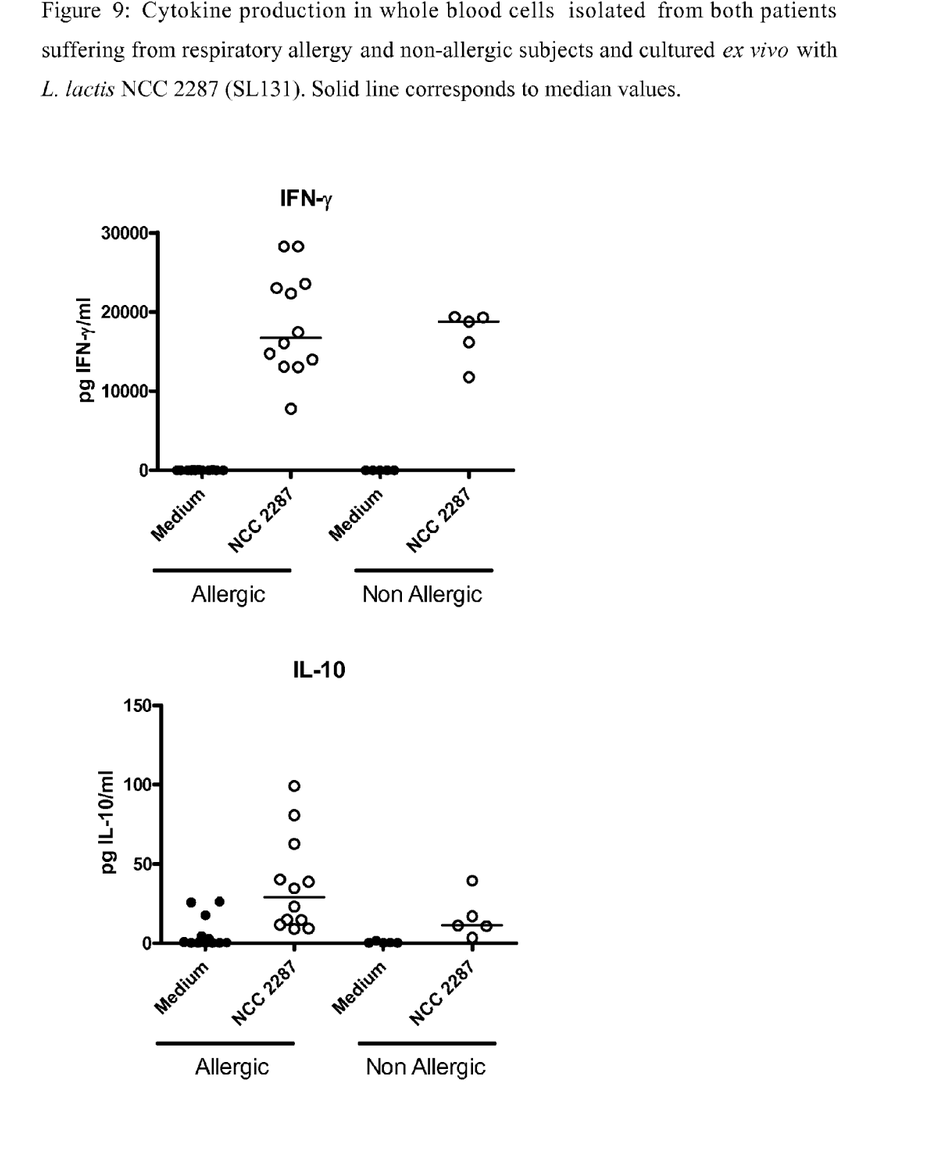
FIG. 9: Cytokine production by whole blood cells from both grass pollen allergic or non-allergic individuals with or without NCC 2287 (SL131) at $10^7$ CFU/ml in culture for 5 days.

In FIG. 9, the effect of *L. lactis* NCC 2287 (SL131) on grass pollen allergic and non-allergic individuals was compared by using a human whole blood assay. FIG. 9 shows that *L. lactis* NCC 2287 (SL131) enhances IFNγ production in both allergic and non-allergic individuals but increases IL-10 levels only in grass-pollen allergics. These results suggest that *L. lactis* NCC 2287 (SL131) has a beneficial effect against respiratory allergens in addition to food allergens. In addition, since IL10 is not increased in non allergic subjects while IFNγ is, NCC 2287 can also boost the immune system in less immuno-competent subjects.

Conclusion: The data show that consumption of *L. lactis* NCC 2287 (SL131) by a sensitized animal leads to reduced allergic symptoms upon exposure to the sensitizing allergen. This effect was specific as consumption of *L. plantarum* NCC 1107 (Lp8) did not have a protective effect. The reduction of symptoms went along with reduced serum levels of MMCP-1 and reduced secretion of cytokines by mesenteric lymph node cells and splenocytes as well as reduced expression of key genes related to allergy in the intestine, suggesting that a modulation of components of the immune system, such as mast-cells and Th2 cells, contributes to the protective effect. A similar effect is expected from the strain SL60.

The second set of data evaluating the effect of *L. lactis* NCC 2287 (SL131) on immune responses triggered via airborne allergens suggests that the strain can exert a similar probiotic effect against respiratory allergies by increasing the production of both IFNγ and IL-10 cytokines as well as inhibiting harmful immune responses (decrease in IL-5) in allergic individuals.

Analytical Methods:

Reagents and Bacterial Biomass:

Bacterial biomass was produced by culture of each strain under standard conditions in liquid cultures. Growth kinetics were determined for each strain and according to these, biomass was harvested 3 h after reaching the stationary phase. At this time-point cultures were washed 2× in cold PBS and frozen in PBS 20% glycerol at −80° C. in 50 μl aliquots. LPS (from *E. coli*) was purchased from Sigma (Buchs, Switzerland).

Isolation and Culture of Th2-Skewed Human PBMC:

Human peripheral blood mononuclear cells (PBMC) were isolated from filters obtained from the "Centre de Transfusion of the CHUV". The cells trapped in the filters were flushed back into the blood collection bag with 90 ml of Hanks balanced salt solution (HBSS) (Sigma). The cells were diluted 1:2 with HBSS and the PBMC were isolated by density gradient centrifugation on Histopaque (Sigma). The cells at the interphase were collected and washed two times with HBSS. The PBMC were resuspended in Iscove's Modified Dulbecco's Medium (cIMDM) (Sigma) complemented with 10% fetal bovine serum FBS (Bioconcept, Paris, France) 1% L-glutamine (Sigma) 1% Penicillin/Streptomycin (Sigma) and 0.1% Gentamycin (Sigma). The cells were cultured in 48 wells plate (Milian, Meyrin, Switzerland) at $1.5 \times 10^6$ cells/ml in the presence of 50 ng/ml of IL-4 (Bioconcept) and 1 μg/ml of anti-CD40 antibody (R&D Systems, Abington, England) in cIMDM to induce a Th2 cytokine phenotype. LPS was used at 1 μg/ml. After 3 days of culture, *L. lactis* NCC 2287 was added at $10^7$, $10^6$, and $10^5$ CFU/ml. After adding ingredients, PBMC culture was continued for an additional 48 h resulting in total culture duration of 5 days.

Isolation and Culture of PBMC from Grass-Allergic Human Donors:

Heparinized, venous blood (50 ml) from male and female adults (18 to 40 years old) with confirmed allergy (allergic rhinoconjunctivitis or asthma) to grass pollen was collected at the beginning of pollen season 24-48 h after the first occurrence of symptoms. PBMC were isolated as described above. Cells were resuspended in RPMI (Sigma) complemented with 8% of human serum AB (Blutspendedienst SRK, Bern, Switzerland) 1% L-glutamine, 1% Penicillin/Streptomycin, 1% of non essential amino acids (Invitrogen, Lucerne, Switzerland), 1% Sodium Pyruvate (Invitrogen) and 0.1% Gentamycin (Sigma). Cells were cultured in 96 wells plate (Milian, Meyrin, Switzerland) at $1 \times 10^6$ cells/ml in three different conditions: 1) in medium 2) in presence of grass allergen pollen extract (ALK-Abello wässrig 6 grass, Volketswil, Switzerland) 3) in presence of 50 ng/ml of IL-4 and 1 μg/ml of anti-CD40. After 2 days of culture, *L. lactis* NCC 2287 was added at $10^7$ CFU/ml. PBMC culture was continued for an additional 3 days resulting in total culture duration of 5 days.

Culture of Whole Blood from Grass-Allergic and Non-Allergic Human Donors

Heparinized, venous blood (10 ml) from male and female adults (18 to 50 years old) with either confirmed allergy (allergic rhinoconjunctivitis or asthma) to grass pollen (clinical history and positive skin prick test) or no allergy (no clinical history and negative skin prick test) was collected both at the start and peak of the pollen season. Whole blood cells (100 μL/well) were resuspended in RPMI (400 μL/well) (Sigma) complemented with 1% L-glutamine, 1% Penicillin/Streptomycin, 1% of non essential amino acids (Invitrogen, Lucerne, Switzerland), and 0.1% Gentamycin (Sigma). Cells were cultured in 48 wells plate (Milian, Meyrin, Switzerland) with or without *L. lactis* NCC 2287 at $10^7$CFU/ml. for 5 days.

Cytokine ELISA:

Human IFN-γ, human IL-5, human IL-10, mouse IFN-γ, mouse IL-13, and mouse IL-10 cytokines were measured using DuoSet kits from R&D systems according to the manufacturer's instructions. Also, human IL-4, IL-5, IL-10, IFN-γ, IL-1β, IL-2, IL-8, TNF-α, IL-12, IL-13 were measured using the human Th1/Th2 10-plex multiplex kit (Meso Scale Discovery, Gaithersburg, USA) according to the manufacturer's instructions.

Evaluation of ELISA Results:

OD values were transformed into pg/ml using the standard curves. To adjust for the large donor-to-donor variation generally observed with PBMC from different human donors, data were standardized according to an arbitrary internal standard. The pg/ml value of IFN-γ obtained for each donor by stimulation with LPS was set to 100%. For normalization of IL-10 values, the amount of IL-10 induced with strain *B. lactis* NCC 2818 (deposited by Nestec SA under CNCM-I3446) was considered as 100%. Finally, the amount of IL-5 induced with IL-4 and anti-CD40 antibody in medium only (i.e. in the absence of probiotics) was set to 100%.

Quantitative Gene Expression Levels by Real-Time PCR:

PBMC ($1.5 \times 10^6$ cells/ml) were cultured in cIMDM with or without IL-4 (50 ng/ml) and anti-CD40 (1 µg/ml) for three days. Thereafter ingredients were added to PBMC and cells were collected after 10 h and 24 h. Total RNA was extracted from stimulated PBMC with SV total RNA isolation system kit (Promega, Wallisellen, Switzerland) including a DNase treatment according to the manufacture's instructions. Total RNA was quantified using the ribogreen RNA quantification kit (Molecular Probes, Basel, Switzerland). Reverse transcription was performed on 1 µg of total RNA by using the Multiscribe Reverse Transcriptase kit (Applied Biosystems, Foster City, Calif., USA). Total RNA was mixed with 50 µM of random hexamers, 0.5 mM of dNTPs, 20 U of RNase inhibitor (Applied Biosystems), 62.5 U of Multiscribe reverse transcriptase, 1× RT buffer, and 5.5 mM of $MgCl_2$ in a final volume of 100 µl. Human IFNγ, IL-10, IL-5, Tbet, GATA3, FoxP3 (Applied Biosystems) were quantified by real time PCR (Applied Biosystems, ABI PRISM 7900HT) using the Taqman gene expression assays. The quantification was normalized with the mean of 3 houses keeping genes: β-actin, GAPDH and HPRT (Applied Biosystems).

Based of the Cycle threshold (Ct) values obtained, a relative and normalized mRNA expression was determined for each gene using the ΔCt. The Ct value for each gene was corrected by the Ct mean of the three house keeping genes. The results were calculated as a relative expression using the formula $2^{-\Delta Ct} \times K$.

OVA Food Allergy Mouse Model:

Six weeks old adult conventional BALB/c mice were sensitized by the oral route (with a gavage needle) at weekly intervals with 20 mg of Ovalbumin (OVA) from Fluka (Buchs, Switzerland)+10 µg/mouse of Cholera toxin (used as adjuvant) from LuBioscience (Lucerne, Switzerland) during 7 weeks. One week after the last sensitization an oral challenge with 100 mg of OVA was performed. Nutritional intervention with *L. lactis* NCC 2287 (SL131) ($5 \times 10^8$ CFU/ml in drinking water) was done at different phases of the experiment; as a primary prevention during sensitisation period or as a secondary prevention starting at the end of the sensitization phase (FIG. 3). Fifteen minutes after challenge mice were individually observed during 30 min. Clinical symptoms were recorded and quantified as follows (Allergic Score): 0: no symptoms, less than 4 episodes of scratching; 1: 4-10 episodes of scratching around the nose and head, no diarrhoea; 2: more than 10 episodes of scratching or bristled fur and immobility or soft stool; 3: diarrhoea or laboured respiration or cyanosis; 4: diarrhoea in combination with immobility after prodding, bristled fur, laboured respiration or cyanosis; 5: anaphylaxis. Four hours after challenge mice were sacrificed (cervical dislocation), blood and the last centimeter of ileum plus one Peyer's patch located in the same area were taken and frozen in liquid nitrogen.

Serum MMCP-1:

Murine mast cells protease 1 (MMCP-1) was quantified in mouse serum by ELISA, purchased from Moredun Scientific (Midlothian, Scotland) according to the manufacture's instructions. The MMCP-1 concentration was obtained by converting OD values in pg/ml using a polynomial standard curve.

Isolation and Culture of Mesenteric Lymph Node (MLN) Lymphocytes:

MLN were homogenized with the plunger of a syringe in a cell strainer (BD Falcon, Milian, Meyrin Switzerland). Cells were centrifuged and washed two times in RPMI (Sigma) complemented with 10% of fetal bovine serum FBS (Biocon-cept, Paris, France), 1% L-glutamine (Sigma), 1% Penicillin/Streptomycin (Sigma), 0.1% Gentamycin (Sigma), 0.1% β-mercaptoethanol (Sigma). Cells were cultured in 96 well flat bottom plate (Corning, Milian) in the absence or presence of OVA at 1000 µg/ml with $3 \times 10^6$ cells/ml. After 72 h of culture plates were frozen.

Cytokines in Supernatant of Mesenteric Lymph Node Cell and Splenocyte Cultures:

Mouse IL-4, IL-5, IL-10, IFN-γ, IL-1β, IL-2, IL-8, TNF-α, IL-12 were measured using the mouse Th1/Th2 9-plex multiplex kit (Meso Scale Discovery, Gaithersburg, USA) according to the manufacture's instructions.

Low Density Array Analyses of Gene Expression in Intestine:

RNA Extraction and Quantification:

Total ribonucleic acids (RNA) from Ileum and Peyer's patch were extracted according to the manufacture's protocol using SV Total RNA isolation System kit purchased from Promega (Dübendorf, Switzerland).

RNA was quantified with quant-IT Ribogreen Reagent kit provided (Promega Dübendorf, Switzerland) according to the manufacture's protocol.

Reverse Transcription:

Reverse transcription was performed on 1 µg of total RNA by using the Multiscribe Reverse Transcriptase kit from Applied Biosystems (Foster City USA). Total RNA was mixed with 50 µM of random hexamers, 0.5 mM of dNTPs, 20 U of RNase inhibitor (Applied Biosystems), 62.5 U of Multiscribe reverse transcriptase, 1× RT buffer, and 5.5 mM of $MgCl_2$ in a final volume of 50 µl. Reverse transcription was run on a T3 thermocycler (Biometra, Göttingen, Germany) with the following cycle program: 10 min at 25° C., 30 min at 48° C., 5 min at 95° C. to finish at 4° C.

Low Density Array (LDA):

Low Density Arrays were designed online on the Applied Biosytems website (http://www3.appliedbiosystems.com/index.htm). The load, the run and the analysis were performed according to the manufacturer's protocol on a quantitative ABI-Prism 7900HT.

The quantification was normalized with the mean of 3 houses keeping genes: β-actin, GAPDH and HPRT. Based on the Cycle threshold (Ct) values obtained, a relative and normalized mRNA expression was determined for each gene using the ΔCt. The Ct value for each gene was corrected by the Ct mean of the three house keeping genes. The results were calculated as a relative expression using the formula $2^{-\Delta Ct \times K}$ were K is a $10^6$ factor. Fold increase results expression was normalized to expression levels in the Negative group.

Example 1

An example of the composition of an infant formula for use according to the present invention is given below. This composition is given by way of illustration only. The protein source is a conventional mix of whey protein and casein.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| *Lactococcus lactis* NCC 2287 (SL131; see experimental part) | $2 \times 10^7$ CFU/g of powder | |

Example 2

Example of the composition of the invention: Adapted milk powder intended for children. This composition is an illustration of the invention.

| Nutrient | per 100 kcal | per liter |
|---|---|---|
| Energy (kcal) | 100 | 670 |
| Protein (g) | 3.66 | 24.5 |
| Fat (g) | 4.52 | 30.2 |
| Linoleic acid (g) | 0.69 | 4.6 |
| α-Linolenic acid (mg) | 73 | 490 |
| Carbohydrates (g) | 11.18 | 74.9 |
| Prebiotic (100% GOS) (g) | 0.64 | 4.3 |
| Na (mg) | 49 | 330 |
| Ca (mg) | 183 | 1220 |
| Vitamin A (µg RE) | 77 | 520 |
| Vitamin D (µg) | 0.99 | 6.6 |
| Vitamin K1 (µg) | 4.7 | 32 |
| Vitamin C (mg) | 9 | 60 |
| Niacin (mg) | 1.6 | 11 |
| Folic acid (µg) | 39 | 260 |
| Fe (mg) | 1.5 | 10 |
| Zn (mg) | 1.2 | 7.9 |
| *Lactococcus lactis* NCC 2287 (SL131; see experimental part) | $2 \times 10^8$ CFU/g of powder | |

Example 3

An example of the composition of a yoghurt drink given to children and adults for use according to the present invention. This composition is an illustration only.

| Nutrient | per 120 kcal |
|---|---|
| Energy (kcal) | 120 |
| Protein (g) | 7.8 |
| Fat (g) | 3.4 |
| Carbohydrates (g) | 14.4 |
| Ca (mg) | 502 |
| Vitamin C (mg) | 17 |
| Vitamin D (IU) | 85 |
| Vitamin K1 (µg) | 4.7 |
| Zinc (mg) | 2 |
| Magnesium (mg) | 29 |
| *Lactococcus lactis* NCC 2287 (SL131; see experimental part) | $2 \times 10^5$ CFU/g of dry-matter (alterative: $5 \times 10^8$ CFU/g of dry-matter) |

Example 4

An example of the composition of a food for pets (cat or dogs) intended for mature pets for use according to the present invention. This composition is an illustration only and may include combinations of nutrients as foreseen in the below:

The compositions include complete foods intended to supply the necessary dietary requirements for an animal or food supplements such as animal treats.

In various embodiments, food compositions such as pet food compositions or pet treat compositions comprise from about 15% to about 50% crude protein.

The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include pork, lamb, equine, poultry, fish, and mixtures thereof.

The food compositions may further comprise from about 5% to about 40% fat. Examples of suitable fats include animal fats and vegetable fats. Preferably the fat source is an animal fat source such as tallow. Vegetable oils such as corn oil, sunflower oil, safflower oil, rape seed oil, soy bean oil, olive oil and other oils rich in monounsaturated and polyunsaturated fatty acids, may also be used. The food compositions may further comprise from about 15% to about 60% carbohydrate. Examples of suitable carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products.

The moisture content for such food compositions varies depending on the nature of the food composition. The food compositions may be dry compositions (e.g., kibble), semi-moist compositions, wet compositions, or any mixture thereof. In a preferred embodiment, the composition is a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one preferred embodiment, the compositions have moisture content from about 5% to about 20%. Dry food products include a variety of foods of various moisture contents, such that they are relatively shelf-stable and resistant to microbial or fungal deterioration or contamination. Also preferred are dry food compositions that are extruded food products such as pet foods or snack foods for either humans or companion animals.

The food compositions may also comprise one or more fiber sources. The term "fiber" includes all sources of "bulk" in the food whether digestible or indigestible, soluble or insoluble, fermentable or nonfermentable. Preferred fibers are from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the present invention to the immune system of an animal.

In some embodiments, the ash content of the food composition ranges from less than 1% to about 15%, preferably from about 5% to about 10%.

In a preferred embodiment, the composition is a food composition with from about 15% to about 50% protein, from about 5% to about 40% fat, from about 5% to about 10% ash content, and having a moisture content of about 5% to about 20%. In other embodiments, the food composition further comprises prebiotics or probiotics as described herein.

The invention claimed is:

1. A method for reducing the symptoms of an allergy originating from food, airborne or cutaneous allergens in a patient having the allergy comprising the step of administering a complete nutritional composition comprising a *Lactococcus* strain to the patient, the *Lactococcus* strain selected from the group consisting of *Lactococcus* lactis NCC 2287 deposited under accession number CNCM-I-4154 and *Lactococcus* lactis NCC 2180 deposited under accession number CNCM-I-4199, wherein the composition comprises an apple extract comprising polyphenols and wherein the apple extract helps in reducing the symptoms of allergies originating from food, airborne or cutaneous allergies.

2. A method for reducing the symptoms of an allergy originating from food, airborne or cutaneous allergens in a patient having the allergy comprising the step of administering a complete nutritional composition comprising a *Lactococcus* strain to the patient, the *Lactococcus* strain selected from the group consisting of *Lactococcus* lactis NCC 2287 deposited under accession number CNCM-I-4154 and *Lactococcus* lactis NCC 2180 deposited under accession number CNCM-I-4199, wherein the *Lactococcus* strain has been inactivated such as to render the *Lactococcus* strain non replicating.

3. The method of claim 2 wherein the complete nutritional composition is administered to the patient having the allergy at least daily for at least a week.

4. The method of claim 3 wherein the composition comprises between $10^4$ and $10^{11}$ colony forming units (CFU) of the *Lactococcus* strain per gram of dry composition.

* * * * *